(12) United States Patent
Genet et al.

(10) Patent No.: US 6,451,068 B1
(45) Date of Patent: Sep. 17, 2002

(54) CATIONIC COMPOUNDS, THEIR USE AS COUPLING AGENTS FOR OXIDATION DYEING OF KERATINOUS FIBERS, DYEING COMPOSITIONS AND DYEING METHODS

(75) Inventors: Alain Genet, Aulnay-sous-Bois; Alain Lagrange, Coupvray, both of (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/646,453

(22) PCT Filed: Mar. 15, 1999

(86) PCT No.: PCT/FR99/00576

§ 371 (c)(1),
(2), (4) Date: Nov. 13, 2000

(87) PCT Pub. No.: WO99/48875

PCT Pub. Date: Sep. 30, 1999

(30) Foreign Application Priority Data

Mar. 20, 1998 (FR) ............................................ 98 03457

(51) Int. Cl.⁷ ................................................. A61K 7/13
(52) U.S. Cl. .................... 8/405; 8/405; 8/406; 8/407; 8/408; 8/409; 8/416; 8/421; 8/423
(58) Field of Search ............................ 8/405, 406, 407, 8/408, 409, 416, 421, 423

(56) References Cited

U.S. PATENT DOCUMENTS

| | | | |
|---|---|---|---|
| 3,100,739 A | 8/1963 | Kaiser et al. ................. | 167/88 |
| 3,442,895 A | 5/1969 | Bugaut et al. ............ | 260/247.1 |
| 3,528,972 A | 9/1970 | Kalopissis et al. ........ | 260/247.1 |
| 4,314,809 A | * 2/1982 | Rose et al. ..................... | 8/406 |
| 4,629,466 A | * 12/1986 | Rose et al. ..................... | 8/408 |
| 4,823,985 A | 4/1989 | Grollier et al. ................. | 222/1 |
| 4,888,025 A | 12/1989 | Bugaut et al. ................. | 8/405 |
| 6,074,438 A | * 6/2000 | Lim et al. ...................... | 8/409 |

FOREIGN PATENT DOCUMENTS

| | | | |
|---|---|---|---|
| BE | 616 439 | 10/1962 | |
| DE | 1 135 589 | 8/1962 | |
| DE | 1 292 784 | 4/1969 | |
| EP | 0 544 400 | 6/1993 | |
| FR | 1 391 675 | 6/1965 | |
| FR | 2 520 358 | 7/1983 | |
| FR | 2 586 913 | 3/1987 | |
| FR | 2 766 178 | 1/1999 | |
| WO | WO 95/01772 | 1/1995 | |
| WO | WO 98/01418 | * 1/1998 | ............ A61K/7/13 |

OTHER PUBLICATIONS

L.K.J. Tong et al., "The Mechanism of Dye Formation in Color Photography. VII. Intermediate Bases in the Deamination of Quinonediimines", Journal of the American Chemical Society, vol. 82, No. 7, Apr. 5, 1960, pp. 1988–1996.

English language Derwent Abstract of FR 2 766 178.

\* cited by examiner

*Primary Examiner*—Yogendra N. Gupta
*Assistant Examiner*—Eisa Elhilo
(74) *Attorney, Agent, or Firm*—Finnegan, Henderson, Farabow, Garrett & Dunner, L.L.P.

(57) ABSTRACT

The invention concerns novel di-benzene compounds comprising at least one cationic group Z, Z being selected among quatemized aliphatic chains, aliphatic chains comprising at least a quatemized saturated cycle, and aliphatic chains comprising at least a quaternized unsaturated cycle, their use as coupling agents in oxidation dyeing of keratinous fibres, dyeing compositions containing same and oxidation dyeing methods using same.

58 Claims, No Drawings

CATIONIC COMPOUNDS, THEIR USE AS COUPLING AGENTS FOR OXIDATION DYEING OF KERATINOUS FIBERS, DYEING COMPOSITIONS AND DYEING METHODS

The invention relates to novel dibenzenic compounds comprising at least one cationic group Z, Z being chosen from quaternized aliphatic chains, aliphatic chains comprising at least one quaternized saturated ring and aliphatic chains comprising at least one quaternized unsaturated ring, to their use as couplers for the oxidation dyeing of keratin fibres, to dye compositions containing them and to oxidation dyeing processes using them.

It is known practice to dye keratin fibres, and in particular human hair, with dye compositions containing oxidation dye precursors, in particular orthophenylenediamines or para-phenylenediamines, orthoaminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

It has already been proposed, in particular in patent application FR-A-2 520 358, to use certain cationic derivatives of meta-phenylenediamines, i.e. more specifically, certain meta-phenylenediamines monosubstituted with a quaternized aliphatic chain, for the oxidation dyeing of keratin fibres in intense shades. However, the use of the meta-phenylenediamines described in that prior patent application does not make it possible to obtain a wide variety of colours and, furthermore, the colorations obtained are not always entirely satisfactory as regards their resistance with respect to the various attacking factors to which the hair may be subjected (the action of light, perspiration, shampooing, etc.).

The Applicant has now discovered, entirely surprisingly and unexpectedly, that dibenzenic compounds of formula (I) defined below comprising at least one cationic group Z, Z being chosen from quaternized aliphatic chains, aliphatic chains comprising at least one quaternized saturated ring, and aliphatic chains comprising at least one quaternized unsaturated ring, are not only suitable for use as a coupler for oxidation dyeing, but also make it possible to obtain dye compositions which give intense colorations, in a very wide range of shades, and which have excellent properties of resistance to the various treatments to which the keratin fibres may be subjected. Finally, these compounds are found to be easy to synthesize.

These discoveries form the basis of the present invention.

A first subject of the invention is thus novel compounds of formula (I) below, and the addition salts thereof with an acid:

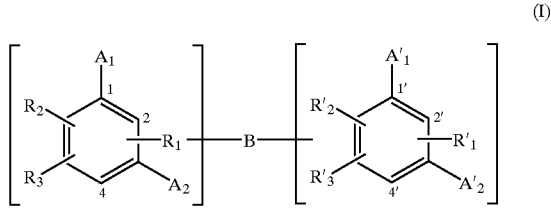

in which:

B is a linker arm which represents an alkyl chain preferably containing from 1 to 14 carbon atoms, which is linear or branched and which can be interrupted by one or more hetero atoms such as oxygen, sulphur or nitrogen atoms, and which is optionally substituted with one or more hydroxyl or $C_1$–$C_6$ alkoxy radicals;

$R_1$, $R_2$, $R_3$, $R'_1$, $R'_2$ and $R'_3$, which may be identical or different, represent a hydrogen atom; a halogen atom; a group Z; a group —CO—Z; a group —CO—OZ; a ($C_1$–$C_6$)alkylcarbonyl radical; an amino($C_1$–$C_6$) alkylcarbonyl radical; an N—Z-amino($C_1$–$C_6$) alkylcarbonyl radical; an N—($C_1$–$C_6$)alkylamino ($C_1$–$C_6$)alkylcarbonyl radical; an N,N-di($C_1$–$C_6$) alkylamino($C_1$–$C_6$)alkylcarbonyl radical; an amino ($C_1$–$C_6$)alkylcarbonyl ($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl($C_1$–$C_6$) alkyl radical; an N,N-di($C_1$–$C_6$)alkylamino($C_1$–$C_6$) alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N—Z-aminosulphonyl radical; a $C_1$–$C_6$ N-alkylaminosulphonyl radical; an N,N-di($C_1$–$C_6$) alkylaminosulphonyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$) alkyl radical; an N,N-di($C_1$–$C_6$)alkylaminosulphonyl ($C_1$–$C_6$)alkyl radical; a carbamyl radical; an N—($C_1$–$C_6$)alkylcarbamyl radical; an N,N-di($C_1$–$C_6$) alkylcarbamyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$) alkoxy($C_1$–$C_6$)alkyl radical; a $C_1$–$C_6$ trifluoroalkyl radical; a cyano radical; a group $OR_6$ or $SR_6$; or an amino group protected with a ($C_1$–$C_6$)alkylcarbonyl, ($C_1$–$C_6$)alkylcarboxyl, trifluoro($C_1$–$C_6$)alkylcarbonyl, amino($C_1$–$C_6$)alkylcarbonyl, N—Z-amino($C_1$–$C_6$) alkylcarbonyl, N—($C_1$–$C_6$)alkylamino($C_1$–$C_6$) alkylcarbonyl, N,N-di($C_1$–$C_6$)alkylamino($C_1$–$C_6$) alkylcarbonyl, ($C_1$–$C_6$)alkylcarboxyl, carbamyl, N—($C_1$–$C_6$)alkylcarbamyl, N,N-di($C_1$–$C_6$) alkylcarbamyl, $C_1$–$C_6$ alkylsulphonyl, aminosulphonyl, N—Z-aminosulphonyl, $C_1$–$C_6$ N-alkylaminosulphonyl, N,N-di($C_1$–$C_6$) alkylaminosulphonyl, thiocarbamyl or formyl radical, a group —CO—Z or a group —CO—OZ;

$R_6$ denotes a $C_1$–$C_6$ alkyl radical; a $C_1$–$C_6$ monohydroxyalkyl radical; a $C_2$–$C_6$ polyhydroxyalkyl radical; a group Z; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy-($C_1$–$C_6$)alkyl radical; a cyano($C_1$–$C_6$)alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$) alkylcarbonyl, formyl, trifluoro-($C_1$–$C_6$)alkylcarbonyl, ($C_1$–$C_6$)alkylcarboxyl, carbamyl, N—($C_1$–$C_6$) alkylcarbamyl, N,N-di-($C_1$–$C_6$)alkylcarbamyl, thiocarbamyl and $C_1$–$C_6$ alkylsulphonyl radicals, and from the groups Z, —CO—Z and —CO—OZ;

$A_1$ represents a group —$NR_4R_5$ or a hydroxyl radical;

$A'_1$ represents a group —$NR'_4R'_5$ or a hydroxyl radical;

$A_2$ represents a group —$NR_7R_8$ or a hydroxyl radical;

$A'_2$ represents a group —$NR'_7R'_8$ or a hydroxyl radical;

$R_4$, $R_5$, $R_7$, $R_8$, $R'_4$, $R'_5$, $R'_7$ and $R'_8$, which may be identical or different, represent a hydrogen atom; a group Z; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a cyano($C_1$–$C_6$)alkyl radical; a carbamyl($C_1$–$C_6$)alkyl radical; an N—($C_1$–$C_6$) alkylcarbamyl($C_1$–$C_6$)alkyl radical; an N,N-di($C_1$–$C_6$) alkylcarbamyl($C_1$–$C_6$)alkyl radical; a thiocarbamyl ($C_1$–$C_6$)alkyl radical; a $C_1$–$C_6$ trifluoroalkyl radical; a $C_1$–$C_6$ sulphoalkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylcarbonyl($C_1$–$C_6$)alkyl radical; a $C_1$–$C_6$ aminoalkyl radical; a $C_1$–$C_6$ aminoalkyl radical in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$) alkylcarbamyl or N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or with a group Z, —CO—Z or —CO—OZ;

one and only one of the radicals $R_4$, $R_5$, $R_7$, $R_8$ and/or one and only one of the radicals $R'_4$, $R'_5$, $R'_7$ and $R'_8$ can also represent a ($C_1$–$C_6$)alkylcarboxyl radical; a ($C_1$–$C_6$) alkylcarbonyl radical; a formyl radical; a trifluoro($C_1$–$C_6$) alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$)alkylcarbonyl radical; a carbamyl radical; an N—($C_1$–$C_6$)alkylcarbamyl radical; an N,N-di($C_1$–$C_6$)alkylcarbamyl radical; a thiocarbamyl radical; an aminosulphonyl radical; an N—Z-aminosulphonyl radical; an N—($C_1$–$C_6$)alkylaminosulphonyl radical; an N,N-di($C_1$–$C_6$)alkylaminosulphonyl radical; a ($C_1$–$C_6$) alkylsulphonyl radical; a group —CO—Z or a group —CO—OZ;

Z is chosen from the unsaturated cationic groups of formulae (II) and (III) below, and the saturated cationic groups of formula (IV) below:

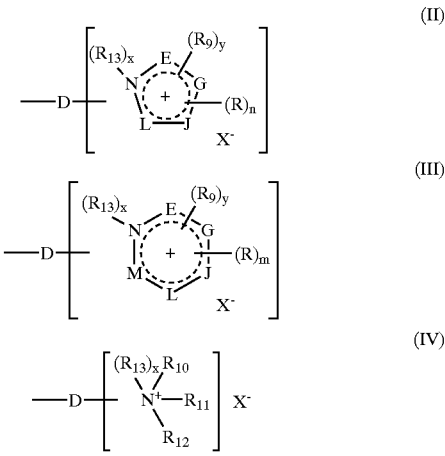

in which:

D is a linker arm which represents a linear or branched alkyl chain preferably containing from 1 to 14 carbon atoms, which may be interrupted by one or more hetero atoms such as oxygen, sulphur or nitrogen atoms, and which may be substituted with one or more hydroxyl or $C_1$–$C_6$ alkoxy radicals;

the ring members E, G, J, L and M, which may be identical or different, represent a carbon, oxygen, sulphur or nitrogen atom;

n is an integer between 0 and 4 inclusive;

m is an integer between 0 and 5 inclusive;

the radicals R, which may be identical or different, represent a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a ($C_1$–$C_6$)alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkylcarbonyl, carbamyl or $C_1$–$C_6$ alkylsulphonyl radical; a group NHR" or NR"R'" in which R" and R'", which may be identical or different, represent a $C_1$–$C_6$ alkyl radical, a $C_1$–$C_6$ monohydroxyalkyl radical or a $C_2$–$C_6$ polyhydroxyalkyl radical;

when n is greater or equal to 2, two of the adjacent radicals R can also form together an unsaturated 5- or 6-membered carbon-based ring or a ring containing one or more hetero atoms;

$R_9$ represents a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri($C_1$–$C_6$)alkylsilane ($C_1$–$C_6$)alkyl radical, a ($C_1$–$C_6$)alkoxy($C_1$–$C_6$)alkyl radical, a carbamyl($C_1$–$C_6$)alkyl radical, a ($C_1$–$C_6$) alkylcarboxy($C_1$–$C_6$)alkyl radical or a benzyl radical;

$R_{10}$, $R_{11}$ and $R_{12}$, which may be identical or different, represent a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy($C_1$–$C_6$)alkyl radical, a cyano($C_1$–$C_6$) alkyl radical, an aryl radical, a benzyl radical, an amido($C_1$–$C_6$)alkyl radical, a tri($C_1$–$C_6$)alkylsilane ($C_1$–$C_6$)alkyl radical or a $C_1$–$C_6$ aminoalkyl radical in which the amine is protected with a ($C_1$–$C_6$) alkylcarbonyl, carbamyl or $C_1$–$C_6$ alkylsulphonyl radical; two of the radicals $R_{10}$, $R_{11}$ and $R_{12}$ can also form, together with the nitrogen atom to which they are attached, a saturated 5- or 6-membered carbon-based ring or a ring containing one or more hetero atoms, such as, for example, a pyrrolidine ring, a piperidine ring, a piperazine ring or a morpholine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$)alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$)alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical;

$R_{13}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or $C_1$–$C_6$ alkylsulphonyl radical; a carboxy($C_1$–$C_6$)alkyl radical; a cyano($C_1$–$C_6$)alkyl radical; a carbamyl ($C_1$–$C_6$)alkyl radical; a $C_1$–$C_6$ trifluoroalkyl radical; a tri($C_1$–$C_6$)alkylsilane ($C_1$–$C_6$)alkyl radical; a sulphonamido($C_1$–$C_6$)alkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a ($C_1$–$C_6$) alkylsulphonyl($C_1$–$C_6$)alkyl radical; a ($C_1$–$C_6$) alkylketo($C_1$–$C_6$)alkyl radical; an N—($C_1$–$C_6$) alkylcarbamyl($C_1$–$C_6$)alkyl radical; an N—($C_1$–$C_6$) alkylsulphonamido($C_1$–$C_6$)alkyl radical;

x and y are integers equal to 0 or 1; with the following conditions:
in the unsaturated cationic groups of formula (II):
when x=0, the linker arm D is attached to the nitrogen atom,
when x=1, the linker arm D is attached to one of the ring members E, G, J or L,
y cannot take the value 1 except:
1) when the ring members E, G, J and L simultaneously represent a carbon atom, and when the radical $R_9$ is borne by the nitrogen atom of the unsaturated ring; or alternatively
2) when at least one of the ring members E, G, J and L represents a nitrogen atom to which the radical $R_9$ is attached;
in the unsaturated cationic groups of formula (III):
when x=0, the linker arm D is attached to the nitrogen atom,
when x=1, the linker arm D is attached to one of the ring members E, G, J, L or M,
y cannot take the value 1 except when at least one of the ring members E, G, J, L and M represents a divalent atom, and when the radical $R_9$ is borne by the nitrogen atom of the unsaturated ring;
in the cationic groups of formula (IV):
when x=0, then the linker arm is attached to the nitrogen atom bearing the radicals $R_{10}$ to $R_{12}$,
when x=1, then two of the radicals $R_{10}$ to $R_{12}$ form, together with the nitrogen atom to which they are attached, a saturated 5- or 6-membered ring as defined above, and the linker arm B is borne by a carbon atom of the said saturated ring;

X⁻ represents a monovalent or divalent anion and is preferably chosen from a halogen atom such as chlorine, bromine, fluorine or iodine, a hydroxide, a hydrogen sulphate or a $C_1$–$C_6$ alkyl sulphate such as, for example, a methyl sulphate or an ethyl sulphate;
it being understood that the number of cationic group Z is at least equal to 1.

As mentioned above, the colorations obtained with the oxidation dye composition in accordance with the invention are strong and produce a wide range of shades and colours. They moreover have excellent properties of resistance to the action of various external agents (light, bad weather, washing, permanent-waving, perspiration, friction). These properties are particularly noteworthy especially as regards resistance of the colorations obtained with respect to the action of light, washing, permanent-waving and perspiration.

In formula (I) above, the alkyl and alkoxy radicals can be linear or branched.

Among the rings of the unsaturated groups Z of formula (II) above, mention may be made in particular, by way of example, of pyrrole, imidazole, pyrazole, oxazole, thiazole, triazole, pyrazolopyrimidium, pyrazolopyridinium, benzoimidazolinium, benzoxazolinium, benzothiazolinium, indolinium, indolidinium, isoindolinium, indazolinium, benzotriazolinium, benzoimidazolindinium and benzopyrimidinium rings.

Among the rings of the unsaturated groups Z of formula (III) above, mention may be made in particular, by way of example, of pyridine, pyrimidine, pyrazine, oxazine, triazine, pyrazolopyridinium, pyrazolopyridinium, quinolinium and tetrahydroquinolinium rings.

Among the compounds of formula (I) above, mention may be made in particular of:
1,4-bis-1-{3-[3-(2,4-diaminophenoxy)propyl]-3H-imidazol-1-ium}butane dichloride monohydrate;
1,3-bis[3-(2,4-diaminophenoxy)propyl]-3H-imidazol-1-ium chloride;
3-[3-(2,4-diaminophenoxy)propyl]-1-[(3-hydroxy-4-methylphenylcarbamoyl)methyl]-3H-imidazol-1-ium chloride;
1,4-bis{3-[(3-hydroxy-4-methylphenylcarbamoyl)methyl]-3H-imidazol-1-ium}butane dichloride;
1,4-bis[3-(2,4-diaminophenoxy)propyl]-1,4-dimethylpiperazine-1,4-diium dichloride;
1,4-bis{3-[2-(2,4-diaminophenyl)ethyl]-3H-imidazol-1-ium}butane dichloride;
1-[3-(2,4-diaminophenoxy)propyl]-4-[(3-hydroxy-4-methylphenylcarbamoyl)methyl]-1,4-dimethylpiperazine-1,4-diium dichloride;
1,4-bis{3-[2-(3-hydroxy-4-methylphenylamino)ethyl]-3H-imidazol-1-ium}butane dibromide;
1,4-bis{3-[(2,4-dihydroxyphenylcarbamoyl)methyl-3H-imidazol-1-ium}butane dichloride;
3-[3-(2,4-diaminophenoxy)propyl]-1-[(2,4-dihydroxyphenylcarbamoyl)methyl]-3H-imidazol-1-ium chloride;
4-[2-(2,4-dihydroxyphenyl)-2-oxoethyl]-1-[2-(3-hydroxy-4-methylphenylamino)ethyl-1,4-dimethylpiperazin-1,4-diium bromochloride;

1,3-bis{[2-(2,4-diaminophenoxy)ethyl] diethylammonium}-propane dibromide;

and the addition salts thereof with an acid.

The compound(s) of formula (I) in accordance with the invention can be readily obtained, according to well-known methods of the prior art, for example by reducing the corresponding cationic nitro compounds (cationic meta-nitroanilines or cationic meta-nitrophenols).

This reduction step (production of a primary aromatic amine), optionally followed by a salification is generally, for the sake of convenience, the last step in the synthesis.

This reduction can take place earlier in the sequence reactions leading to the preparation of the compounds of formula (I), and according to well-known processes, in which case it is necessary to "protect" the primary amine created (for example by means of an acetylation, benzenesulphonation, etc. step) then carry out the desired substitution(s) or modification(s) (including the quarternization)and end by "deprotection" (generally in acidic medium) of the amine function.

Similarly, the phenolic function can be protected according to well-known processes, with a benzyl radical ("deprotection" by catalytic reduction) or with an acetyl or mesyl radical("deprotection" in acidic medium).

When the synthesis is complete, the compounds of formula (I) in accordance with the invention can, if necessary, be recovered by methods that are well-known in the prior art, such as crystallization or distillation.

Another subject of the invention is the use of the compounds of formula (I) in accordance with the invention as couplers for the oxidation dyeing of keratin fibres, and in particular of human keratin fibres such as the hair.

A subject of the invention is also a composition for the oxidation dyeing of keratin fibres, and in particular of human keratin fibres such as the hair, characterized in that it comprises, as coupler, in a medium which is suitable for dyeing, at least one compound of formula (I) in accordance with the invention.

The compound(s) of formula (I) in accordance with the invention and/or the addition salt(s) thereof with an acid preferably represent(s) from 0.0005 to 12% by weight approximately relative to the total weight of the dye composition, and even more preferably from 0.005 to 6% by weight approximately relative to this weight.

According to one preferred embodiment of the invention, the dye composition also includes one or more oxidation bases which can be chosen from the oxidation bases conventionally used in oxidation dyeing and among which mention may be made in particular of para-phenylenediamines, bis(phenyl)alkylenediamines, para-aminophenols, ortho-aminophenols and heterocyclic bases.

Among the para-phenylenediamines which can be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-5 amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(β-hydroxyethyl)-para-phenylenediamine, N—(β,γ-dihydroxypropyl)-para-phenylenediamine, N—(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N—(β-methoxyethyl)-para-phenylenediamine, and the addition salts thereof with an acid.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino- 6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

When they are used, these oxidation bases preferably represent(s) from 0.0005 to 12% by weight approximately relative to the total weight of the dye composition, and even more preferably from 0.005 to 6% by weight approximately relative to this weight.

In addition to the compound(s) of formula (I) above, the dye composition in accordance with the invention can also include one or more additional couplers which can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N—(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3- diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represents from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (compounds of formula (I), additional oxidation bases and couplers) are chosen in particular from the hydrochlorides, hydrobromides, sulphates, citrates, succinates, tartrates, lactates and acetates.

The medium-which is suitable for dyeing (or support) generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which can be mentioned, for example, are aqueous ammonia, alkaline carbonates, alkanolamines such as mono-, di- and triethanolamine and derivatives thereof, sodium hydroxide, potassium hydroxide and the compounds of formula (V) below:

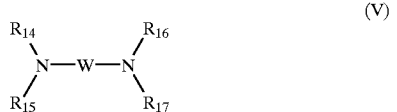

(V)

in which W is a propylene residue optionally substituted with a hydroxyl group or a $C_1$–$C_6$ alkyl radical; $R_{14}$, $R_{15}$, $R_{16}$ and $R_{17}$, which may be identical or different, represent a hydrogen atom, a $C_1$–$C_6$ alkyl radical or a $C_1$–$C_6$ hydroxyalkyl radical.

The oxidation dye compositions in accordance with the invention can also include at least one direct dye, in particular in order to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compound(s) such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for the oxidation dyeing of keratin fibres, and in particular of human keratin fibres such as the hair, using the dye composition as defined above.

According to this process, at least one dye composition as defined above is applied to the fibres, the colour being developed at acidic, neutral or alkaline pH using an oxidizing agent which is added, just at the time of use, to the dye composition, or which is present in an oxidizing composition that is applied simultaneously or sequentially.

According to a preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates, persalts such as perborates and persulphates, and enzymes such as peroxidases and 2-electron oxidoreductases. Hydrogen peroxide is particularly preferred.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2 586 913 in the name of the Applicant.

The examples which follow are intended to illustrate the invention without thereby limiting its scope.

PREPARATION EXAMPLE

Synthesis of 1,4-bis-1-{3-[3-(2,4-Diaminophenoxy)propyl]-3H-imidazol-1-ium]butane Dichloride Tetrahydrochloride Monohydrate

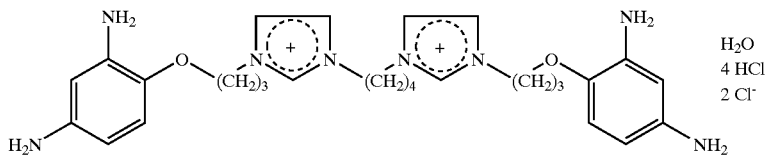

a) Synthetic Preparation of N-[2-(3-Chloropropoxy)-5-nitrophenyl]acetamide

A mixture of 186.5 g (0.94 mol) of N—(2-hydroxy-5-nitrophenyl)acetamide and 142.7 g (1.03 mol) of potassium carbonate in 570 ml of dimethylformamide was heated to 30–35° C. with stirring; 444.0 g (2.82 mol of 1-bromo-3-chloropropane were then added and heating was continued at 40° C. for 7 hours (orange-coloured suspension).

The reaction mixture was poured into 3 litres of ice-cold water and the crystalline precipitate was spin-filtered, reslurried in water and then in isopropyl alcohol and dried under vacuum at 40° C. over phosphorus pentoxide.

After purification by recrystallization from refluxing isobutanol, 203.0 g of beige-coloured crystals were obtained, which melted at 134° C. (Kofler)and the elemental analysis of which, calculated for $C_{11}H_{13}N_2O_4Cl$, was:

| %          | C     | H    | N     | O     | Cl    |
|------------|-------|------|-------|-------|-------|
| Calculated | 48.45 | 4.81 | 10.27 | 23.47 | 13.00 |
| Found      | 48.58 | 4.79 | 10.25 | 23.50 | 13.20 | b) Ouaternization of N-[2-(3-Chloropropoxy)-5-nitrophenyl]acetamide 43.6 g (0.16 mol) of N-[2-(3-chloropropoxy)-5-nitrophenyl]acetamide obtained above in the preceding step and 15.2 g (0.08 mol) of 1,4-diimidazol-1-ylbutane in 130 ml of 2-methyl-1-propanol were refluxed for 15 hours.

The mixture was cooled to room temperature and the oily precipitate was separated out by settling and taken up in absolute ethanol to the point of crystallization.

After spin-filtering, recrystallization from refluxing 96° ethanol and drying at 40° C. over potassium hydroxide, 28.0 g of pale yellow crystals were obtained, which melted at 135° C. (Kofler)and the elemental analysis of which, calculated for $C_{32}H_{40}N_8O_8Cl_2 \cdot 2H_2O$, was:

| %          | C     | H    | N     | O     | Cl   |
|------------|-------|------|-------|-------|------|
| Calculated | 49.81 | 5.75 | 14.52 | 20.73 | 9.19 |
| Found      | 49.39 | 5.84 | 14.48 | 20.53 | 9.10 | c) Preparation of 1,4-bis-1-{3-[3-(2-Acetamino-4-aminophenoxy)propyl]-3H-imidazol-1-ium}butane 27.5 g (0.0356 mol) of the compound obtained above in the preceding step, 7 g of 5% palladium-on-charcoal (containing 50% water), 150 ml of 96° ethanol and 150 ml of water were placed in a hydrogenator.

The reduction took place over half an hour under a hydrogen pressure of about 8 bar and at a temperature which was raised gradually to 75° C. After filtering off the catalyst under nitrogen, the filtrate was evaporated to dryness under reduced pressure.

The crystalline compound obtained was purified by recrystallization from a reflexing ethanol/water mixutre.

21.8 g of off-white crystals were obtained, which melted at 106–108° C. (Kofler).

d) Deacetylation of 1,4-bis-1-{3-[3-(2-Acetamino-4-aminophenoxy)propyl]-3H-imidazol-1-ium}butane A solution of 20.2 g (0.0299 mol) of 1,4-bis-1-{3-[3-(2-acetamino-4-aminophenoxy)propyl]-3H-imidazol-1-ium}butane, obtained above in the preceding step, in 40 ml of aqueous 36% hydrochloric acid was heated for 1 hour on a boiling water bath.

The reaction mixture was cooled in a bath of ice, diluted with 80 ml of absolute ethanol, spin-filtered, washed with absolute ethanol and dried at 45° C. under vacuum and over potassium hydroxide.

18.0 g of white crystals of 1,4-bis-1-{3-[3-(2,4-diaminophenoxy)propyl]-3H-imidazol-1-ium]butane dichloride tetrahydrochloride monohydrate were obtained, which melted with decomposition at more than 260° C. (Kofler) and the elemental analysis of which, calculated for $C_{28}H_{44}N_8O_2Cl_6 \cdot H_2O$, was:

| %          | C     | H    | N     | O    | Cl    |
|------------|-------|------|-------|------|-------|
| Calculated | 44.52 | 6.14 | 14.83 | 6.35 | 28.16 |
| Found      | 44.45 | 6.31 | 14.49 | 6.86 | 28.49 |

APPLICATION EXAMPLES

Examples 1 and 2 of Dyeing in Basic Medium

The dye compositions below were prepared (contents in grams):

| EXAMPLE | 1 | 2 |
|---|---|---|
| 1,4-Bis-1-{3-[3-(2,4-diaminophenoxy)propyl]-3H-imidazol-1-ium}butane dichloride tetrahydrochloride monohydrate (compound of formula (I)) | 1.13 | 1.13 |
| para-Phenylenediamine (oxidation base) | 0.324 | — |
| para-Aminophenol (oxidation base) | — | 0.327 |
| Common dye support | (*) | (*) |
| Demineralized water qs | 100 g | 100 g |

-continued

| EXAMPLE | 1 | 2 |
|---|---|---|
| (*) Common dye support: | | |
| 96° ethyl alcohol | 18 g | |
| Sodium metabisulphite as an aqueous 35% solution | 0.68 g | |
| Pentasodium salt of diethylenetriaminepentaacetic acid | 1.1 g | |
| Aqueous ammonia containing 20% $NH_3$ | 10.0 g | |
| Demineralized water qs | 100 g | |

At the time of use each, each of the above dye compositions was mixed weight for weight with a 20-volume hydrogen peroxide solution (6% by weight) of pH 3.

The mixture obtained was applied to locks of natural or permanent-waved grey hair containing 90% white hairs, for 30 minutes. The locks were then rinsed, washed with a standard shampoo, rinsed again and then dried.

The shades obtained are given in the table below:

| EXAMPLE | DYEING pH | Shade obtained |
|---|---|---|
| 1 | 10 ± 0.2 | Matt-blue light chestnut |
| 2 | 10 ± 0.2 | Ash-red light chestnut |

What is claimed is:

1. At least one compound of formula (I). or at least one acid addition salt thereof, or a mixture thereof:

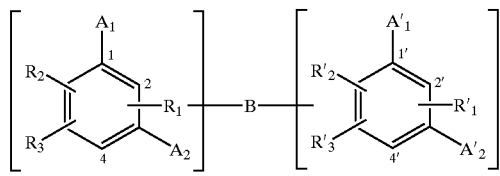

(I)

in which:
B is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1-C_6$ alkoxy groups;

$R_1$, $R_2$, $R_3$, $R'_1$, $R'_2$ and $R'_3$, which may be identical or different, are each chosen from hydrogen; halogens; Z groups; —CO—Z groups; —CO—OZ groups; ($C_1-C_6$) alkylcarbonyl groups; amino($C_1-C_6$)alkylcarbonyl groups; N—Z-amino($C_1-C_6$)alkylcarbonyl groups; N—($C_{1-6}$)alkyl-amino($C_1-C_6$)alkylcarbonyl groups; N,N-di($C_1-C_6$)alkylamino($C_{1-6}$)alkylcarbonyl groups; amino($C_1-C_6$)alkylcarbonyl($C_1-C_6$)alkyl groups; N—Z-amino($C_{1-6}$)alkylcarbonyl($C_1-C_6$)alkyl groups; N—($C_1-C_6$)alkylamino($C_1-C_6$)alkylcarbonyl($C_1-C_6$) alkyl groups; N,N-di($C_1-C_6$)alkylamino($C_1-C_6$) alkylcarbonyl($C_1-C_6$)alkyl groups; a carboxyl group; ($C_1-C_6$)alkylcarboxyl groups; $C_1-C_6$ alkylsulphonyl groups; aminosulphonyl groups; N—Z-aminosulphonyl groups; $C_1-C_6$ N-alkylaminosulphonyl groups; N,N-di($C_{1-6}$) alkylamino-sulphonyl groups; $C_1-C_6$ aminosulphonylalkyl groups; $C_1-C_6$ N—Z-aminosulphonylalkyl groups; N—($C_1-C_6$)alkylaminosulphonyl($C_1-C_6$)alkyl groups; N,N-di($C_1-C_6$)alkylaminosulphonyl($C_1-C_6$) alkyl groups; a carbamyl group; N—($C_{1-6}$) alkylcarbamyl groups; N,N-di($C_1-C_6$)alkylcarbamyl groups; carbamyl($C_1-C_6$)alkyl groups; N—($C_1-C_6$) alkylcarbamyl($C_1-C_6$)alkyl groups; N,N-di($C_1-C_6$) alkylcarbamyl($C_1-C6$)alkyl groups; $C_1-C_6$ alkyl groups; $C_1-C_6$ monohydroxyalkyl groups; $C_2-C_6$ polyhydroxyalkyl groups; ($C_1-C_6$)alkoxy($C_1-C_6$)alkyl groups; $C_1-C_6$ trifluoroalkyl groups; a cyano group; groups —$OR_6$; groups —$SR_6$; and amino groups protected with at least one group chosen from ($C_1-C_6$) alkylcarbonyl groups, ($C_1-C_6$)alkylcarboxyl groups, trifluoro($C_1-C_6$)alkylcarbonyl groups, amino($C_1-C_6$) alkylcarbonyl groups, N—Z-amino($C_1-C_6$) alkylcarbonyl groups, N—($C_1-C_6$)alkylamino($C_1-C_6$) alkylcarbonyl groups, N,N-di($C_1-C_6$)alkylamino ($C_1-C_6$)alkylcarbonyl groups, ($C_1-C_6$)alkylcarboxyl groups, a carbamyl group, N—($C_1-C_6$)alkylcarbamyl groups, N,N-di($C_{1-6}$)alkylcarbamyl groups, $C_1-C_6$ alkylsulphonyl groups, aminosulphonyl groups, N—Z-aminosulphonyl groups, $C_1-C_6$ N-alkylaminosulphonyl groups, N,N-di($C_1-C_6$) alkylaminosulphonyl groups, a thiocarbamyl group, a formyl group, —CO—Z groups, and —CO—OZ groups;

$R_6$ is chosen from $C_1-C_6$ alkyl groups; $C_1-C_6$ monohydroxyalkyl groups; $C_2-C_6$ polyhydroxyalkyl groups; groups Z; ($C_1-C_6$)alkoxy($C_1-C_6$)alkyl groups; aryl groups; a benzyl group; carboxy($C_1-C_6$)alkyl groups; ($C_1-C_6$)alkylcarboxy-($C_1-C_6$)alkyl groups; cyano ($C_1-C_6$)alkyl groups; carbamyl($C_1-C_6$)alkyl groups; N—($C_{1-6}$)alkylcarbamyl($C_1-C_6$)alkyl groups; N,N-di ($C_1-C_6$)alkylcarbamyl($C_1-C_6$)alkyl groups; $C_{1-6}$ trifluoroalkyl groups; $C_1-C_6$ aminosulphonylalkyl groups; $C_1-C_6$ N—Z-aminosulphonylalkyl groups; N—($C_1-C_6$)alkylaminosulphonyl($C_1-C_6$)alkyl groups; N,N-di($C_{1-6}$)alkylaminosulphonyl-($C_{1-6}$)alkyl groups;($C_1-C_6$)alkylsulphinyl($C_1-C_6$)alkyl groups; ($C_1-C_6$)alkylsulphonyl($C_1-C_6$)alkyl groups;($C_1-C_6$) alkylcarbonyl($C_{1-6}$)alkyl groups; $C_1-C_6$ aminoalkyl groups; $C_1-C_6$ aminoalkyl groups wherein said amino is substituted with one or two groups chosen from $C_1-C_6$ alkyl groups, $C_1-C_6$ monohydroxyalkyl groups, $C_2-C_6$ polyhydroxyalkyl groups, ($C_1-C_6$) alkylcarbonyl groups, a formyl group, trifluoro-($C_{1-6}$) alkylcarbonyl groups, ($C_1-C_6$)alkylcarboxyl groups, a carbamyl group, N—($C_{1-6}$)alkylcarbamyl groups, N,N-di-($C_1-C_6$)alkylcarbamyl groups, a thiocarbamyl group, $C_1-C_6$ alkylsulphonyl groups, Z groups, —CO—Z groups, and —CO—OZ groups;

$A_1$ is chosen from -$NR_4R_5$ groups and a hydroxyl group;
$A'_1$ is chosen from -$NR'_4R'_5$ groups and a hydroxyl group;
$A_2$ is chosen from -$NR_4R_5$ groups and a hydroxyl group;
$A'_2$ is chosen from -$NR'_4R'_5$ groups and a hydroxyl group;
$R_4$, $R_5$, $R_7$, $R_8$, $R'_4$, $R'_5$, $R'_7$ and $R'_8$, which may be identical or different, are each chosen from hydrogen; Z groups; $C_1-C_6$ alkyl groups; $C_1-C_6$ monohydroxyalkyl groups; $C_2-C_6$ polyhydroxyalkyl groups; ($C_1-C_6$) alkoxy($C_1-C_6$)alkyl groups; aryl groups; a benzyl group; cyano($C_1-C_6$)alkyl groups; carbamyl($C_1-C_6$) alkyl groups; N—($C_1-C_6$)alkylcarbamyl($C_1-C_6$)alkyl groups; N,N-di($C_{1-6}$)alkylcarbamyl($C_1-C_6$)alkyl groups; thiocarbamyl($C_1-C_6$)alkyl groups; $C_1-C_6$ trifluoroalkyl groups; $C_1-C_6$ sulphoalkyl groups; ($C_1-C_6$) alkylcarboxy($C_1-C_6$)alkyl groups; ($C_{1-6}$)

alkylsulphinyl-$(C_1-C_6)$alkyl groups; $C_1-C_6$ aminosulphonylalkyl groups; $C_1-C_6$ N—Z-aminosulphonylalkyl groups; N—$(C_1-C_6)$alkylaminosulphonyl$(C_1-C_6)$alkyl groups; N,N-di$(C_1-C_6)$alkylaminosulphonyl$(C_1-C_6)$alkyl groups; $(C_1-C_6)$alkylcarbonyl$(C_1-C_6)$alkyl groups; $C_1-C_6$ aminoalkyl groups; $C_1-C_6$ aminoalkyl groups wherein said amino is substituted with one or two groups chosen from $C_1-C_6$ alkyl groups, $C_1-C_6$ monohydroxyalkyl groups, $C_2-C_6$ polyhydroxyalkyl groups, $(C_1-C_6)$alkylcarbonyl groups, a carbamyl group, N—$(C_1-C_6)$alkylcarbamyl groups, N,N-di$(C_1-C_6)$alkylcarbamyl groups, $C_1-C_6$ alkylsulphonyl groups, a formyl group, trifluoro$(C_1-C_6)$alkylcarbonyl groups, $(C_1-C_6)$alkylcarboxyl groups, thiocarbamyl groups, Z groups, —CO—Z groups, and —CO—OZ groups;

one of the groups $R_4$, $R_5$, $R_7$ and $R_8$ or one of the groups $R'_4$, $R'_5$, $R'_7$ and $R'_8$, or combinations thereof, which may be identical or different, are optionally chosen from $(C_1-C_6)$alkylcarboxyl groups; $(C_1-C_6)$alkylcarbonyl groups; a formyl group; trifluoro$(C_1-C_6)$alkylcarbonyl groups; amino$(C_1-C_6)$alkylcarbonyl groups; N—Z-amino$(C_1-C_6)$alkylcarbonyl groups; N—$(C_1-C_6)$alkylamino$(C_1-C_6)$alkylcarbonyl groups; N,N-di$(C_1-C_6)$alkylamino$(C_1-C_6)$alkylcarbonyl groups; a carbamyl group; N—$(C_1-C_6)$alkylcarbamyl groups; N,N-di$(C_1-C_6)$alkylcarbamyl groups; a thiocarbamyl group; an aminosulphonyl group; N—Z-aminosulphonyl groups; N—$(C_1-C_6)$alkylaminosulphonyl groups; N,N-di$(C_1-C_6)$alkylaminosulphonyl groups;$(C_1-C_6)$alkylsulphonyl groups; —CO—Z groups; and—CO—OZ groups Z, which may be identical or different, is chosen from unsaturated cationic groups of formula (II), unsaturated cationic groups of formula (III), and saturated cationic groups of formula (IV):

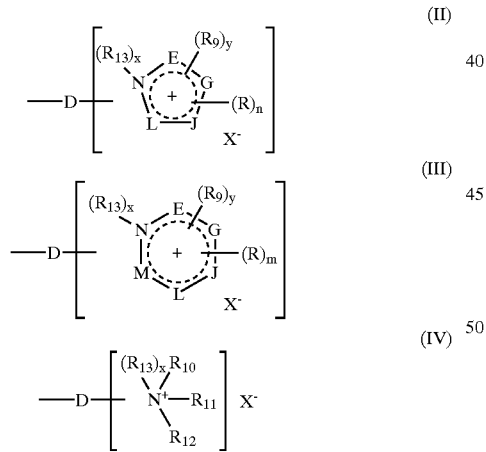

in which:
D is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1-C_6$ alkoxy groups;

ring members E, G, J, L and M, which may be identical or different, are each chosen from carbon, oxygen, sulphur, and nitrogen;

n is an integer chosen from 0 to 4 inclusive;

m is an integer chosen from 0 to 5 inclusive;

the groups R, which may be identical or different, are each chosen from additional Z groups which may be identical to or different from other Z groups, halogens, hydroxyl groups, $C_1-C_6$ alkyl groups, $C_1-C_6$ monohydroxyalkyl groups, $C_2-C_6$ polyhydroxyalkyl groups, a nitro group, a cyano group, cyano$(C_1-C_6)$alkyl groups, $C_1-C_6$ alkoxy groups, tri$(C_1-C_6)$alkylsilane$(C_1-C_6)$alkyl groups, an amino group, an aldehydo group, a carboxyl group, $(C_1-C_6)$alkylcarbonyl groups, a thio group, $C_1-C_6$ thioalkyl groups, $C_1-C_6$ alkylthio groups, an amino group, amino groups protected with at least one group chosen from $(C_1-C_6)$alkylcarbonyl groups, a carbamyl group, and $C_1-C_6$ alkylsulphonyl groups, and NHR" groups and NR"R'" groups wherein R" and R'", which may be identical or different, are each chosen from $C_1-$, alkyl groups, $C_1-C_6$ monohydroxyalkyl groups and $C_2-C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_9$ is chosen from $C_1-C_6$ alkyl groups, $C_1-C_6$ monohydroxyalkyl groups, $C_2-C_6$ polyhydroxyalkyl groups, cyano$(C_1-C_6)$alkyl groups, tri$(C_1-C_6)$alkylsilane$(C_1-C_6)$alkyl groups, $(C_1-C_6)$alkoxy$(C_1-C_6)$alkyl groups, carbamyl$(C_1-C_6)$alkyl groups, $(C_{1-6})$alkylcarboxy$(C_1-C_6)$alkyl groups, and a benzyl group;

$R_{10}$, $R_{11}$ and $R_{12}$, which may be identical or different, are each chosen from $C_1-C_6$ alkyl groups, $C_1-C_6$ monohydroxyalkyl groups, $C_2-C_6$ polyhydroxyalkyl groups, $(C_1-C_6)$alkoxy$(C_1-C_6)$alkyl groups, cyano$(C_1-C_6)$ alkyl groups, aryl groups, a benzyl group, $C_1-C_6$ amidoalkyl groups, tri$(C_1-C_6)$alkylsilane$(C_1-C_6)$alkyl groups, and $C_1-C_6$ aminoalkyl groups wherein said amino is protected with at least one group chosen from $(C_1-C_6)$alkylcarbonyl groups, a carbamyl group and $C_1-C_6$ alkylsulphonyl groups; two of said groups $R_{10}$, $R_{11}$ and $R_{12}$, can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1-C_6$ alkyl groups, $C_1-C_6$ monohydroxyalkyl groups, $C_2-C_6$ polyhydroxyalkyl groups, a nitro group, a cyano group, cyano$(C_1-C_6)$alkyl groups, $C_1-C_6$ alkoxy groups, tri$(C_{1-6})$alkylsilane$(C_1-C_6)$alkyl groups, amino group, an aldehydo group, a carboxyl group, keto$(C_1-C_6)$alkyl groups, a thio group, $C_1-C_6$ thioalkyl groups, $C_1-C_6$ alkylthio groups, an amino group, and amino groups protected with at least one group chosen from $(C_1-C_6)$alkylcarbonyl groups, a carbamyl group and $C_1-C_6$ alkylsulphonyl groups;

$R_{13}$ is chosen from $C_1-C_6$ alkyl groups, $C_{1-6}$ monohydroxyalkyl groups, $C_2-C_6$ polyhydroxyalkyl groups, aryl groups, a benzyl group, $C_1-C_6$ aminoalkyl groups, carboxy$(C_1-C_6)$alkyl groups, cyano$(C_1-C_6)$alkyl groups, carbamyl$(C_{1-6})$alkyl groups, $C_1-C_6$ trifluoroalkyl groups, tri$(C_1-C_6)$alkylsilane$(C_1-C_6)$alkyl groups, $C_1-C_6$ sulphonamidoalkyl groups, $(C_1-C_6)$alkylcarboxy$(C_1-C_6)$alkyl groups, $(C_1-C_6)$alkylsulphinyl$(C_1-C_6)$alkyl groups, $(C_1-C_6)$alkylsulphonyl$(C_1-C_6)$alkyl groups, $(C_1-C_6)$alkylketo ($C_1$-$C_6$)alkyl groups, N—($C_1$-$C_6$)-alkylcarbamyl ($C_1$-$C_6$)alkyl groups, N—($C_1$-$C_6$)alkylsulphonamido ($C_1$-$C_6$)alkyl groups, and $C_1$-$C_6$ aminoalkyl groups wherein said amino is protected with at least one group chosen from ($C_1$-$C_6$)alkylcarbonyl groups, a carbamyl group and $C_1$-$C_6$ alkylsulphonyl groups;

x and y, which may be identical or different, are integers chosen from 0 and 1;

$X^-$ is chosen from a monovalent anion and a divalent anion; and provided that:
when Z is an unsaturated cationic group of formula (II):
if x=0, then said linker arm D is attached to said nitrogen atom other than E, G, J, and L,
if x=1, then said linker arm D is attached to one of said ring members chosen from E, G, J and L,
y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached;
when Z is an unsaturated cationic group of formula (III):
if x=0, then said linker arm D is attached to said nitrogen atom other than E, G, J, L, and M,
if x=1, then said linker arm D is attached to one of said ring members chosen from E, G, J, L, and M,
y=1 only when at least one of said ring members E, G, J, L and M is a divalent atom and $R_7$ is attached to said nitrogen atom of the unsaturated ring other than E, G, J, L and M; and
when Z is a cationic group of formula (IV):
if x=0, then the linker arm D is attached to the nitrogen atom bearing said groups $R_8$, $R_9$ and $R_{10}$;
if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;
wherein at least one of $R_1$, $R_2$, $R_3$, $R_4$, $R_5$, $R_6$, $R_7$, $R_8$, $R'_1$, $R'_2$, $R'_3$, $R'_4$, $R'_5$, $R'_7$, and $R'_8$ comprises a Z group.

2. At least one compound, acid addition salt or mixture, according to claim 1, wherein B is a linker arm comprising from 1 to 14 carbon atoms.

3. At least one compound, acid addition salt, or mixture, according to claim 1, wherein B is a linker arm interrupted by at least one heteroatom chosen from oxygen, sulphur, and nitrogen.

4. At least one compound, acid addition salt, or mixture, according to claim 1, wherein D is a linker arm comprising from 1 to 14 carbon atoms.

5. At least one compound, acid addition salt, or mixture, according to claim 1, wherein D is a linker arm interrupted by at least one heteroatom chosen from oxygen, sulphur, and nitrogen.

6. At least one compound, salt, or mixture according to claim 1, wherein said said ring of said unsaturated cationic groups Z of formula (II) is chosen from a pyrrole ring, an imidazole ring, a pyrazole ring, an oxazole ring, a thiazole ring, a triazole ring, a pyrazolopyrimidinium ring, a pyrazolopyridinium ring, a benzoimidazolinium ring, a benzoxazolinium ring, a benzothiazolinium ring, an indolinium ring, an indolidinium ring, an isoindolinium ring, an indazolinium ring, a benzotriazolinium ring, a benzoimidazolidinium ring and a benzopyrimidinium ring.

7. At least one compound, salt, or mixture according to claim 1, wherein said ring of said unsaturated cationic groups Z of formula (III) is chosen from a pyridine ring, a pyrimidine ring, a pyrazine ring, an oxazine ring, a triazine ring, a pyrazolopyrimidinium ring, a pyrazolopyridinium ring, a quinolinium ring and a tetrahydroquinolinium ring.

8. At least one compound, salt, or mixture according to claim 1, wherein two of said groups $R_{10}$, $R_{11}$ and $R_{12}$ form a ring chosen from a pyrrolidine ring, a piperidine ring, a piperazine ring and a morpholine ring.

9. At least one compound, salt, or mixture according to claim 1, wherein said $X^-$ is chosen from a halogen atom, a hydroxide group, a hydrogen sulphate group and a $C_1$-$C_6$ alkyl sulphate group.

10. At least one compound chosen from:
1,4-bis-1-{3-[3-(2,4-diaminophenoxy)propyl]-3H-imidazol-1-ium}butane dichloride monohydrate;
1,3-bis[3-(2,4-diaminophenoxy)propyl]-3H-imidazol-1-ium chloride;
3-[3-(2,4-diaminophenoxy)propyl]-1-[(3-hydroxy-4-methylphenylcarbamoyl)methyl]-3H-imidazol-1-ium chloride;
1,4-bis{3-[(3-hydroxy-4-methylphenylcarbamoyl) methyl]-3H-imidazol-1-ium}butane dichloride;
1,4-bis[3-(2,4-diaminophenoxy)propyl]-1,4-dimethylpiperazine-1,4-diium dichloride;
1,4-bis{3-[2-(2,4-diaminophenyl)ethyl]-3H-imidazol-1-ium}butane dichloride;
1-[3-(2,4-diaminophenoxy)propyl]-4-[(3-hydroxy-4-methylphenylcarbamoyl)methyl]-1,4-dimethylpiperazine-1,4-diium dichloride;
1,4-bis{3-[2-(3-hydroxy-4-methylphenylamino)ethyl]-3H-imidazol-1-ium}butane dibromide;
1,4-bis{3-[(2,4-dihydroxyphenylcarbamoyl)methyl-3H-imidazol-1-ium}butane dichloride;
3-[3-(2,4-diaminophenoxy)propyl]-1-[(2,4-dihydroxyphenylcarbamoyl)methyl]-3H-imidazol-1-ium chloride;
4-[2-(2,4-dihydroxyphenyl)-2-oxoethyl]-1-[2-(3-hydroxy-4-methylphenylamino)ethyl-1,4-dimethylpiperazine-1,4-diium bromochloride;
1,3-bis{[2-(2,4-diaminophenoxy)ethyl] diethylammonium}propane dibromide; or at least one acid addition salt thereof; or a mixture thereof.

11. At least one coupler for oxidation dyeing of keratin fibres chosen from compounds of formula (1) and acid addition salts thereof:

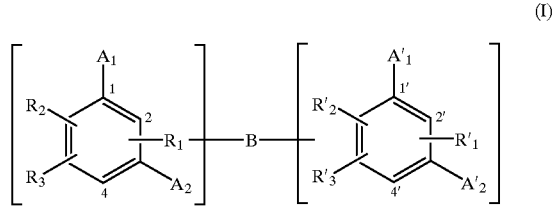

(I)

in which:
B is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$-$C_6$ alkoxy groups;

$R_1$, $R_2$, $R_3$, $R'_1$, $R'_2$ and $R'_3$, which may be identical or different, are each chosen from hydrogen; halogens; Z groups; —CO—Z groups; —CO—OZ groups; ($C_1$–$_6$) alkylcarbonyl groups; amino($C_1$–$C_6$)alkylcarbonyl groups; N—Z-amino($C_1$–$C_6$)alkylcarbonyl groups; N—($C_1$–$_6$)alkylamino($C_1$–$C_6$)alkylcarbonyl groups; N,N-di($C_1$–$C_6$)alkylamino($C_1$–$_6$)alkylcarbonyl groups; amino($C_1$–$C_6$)alkylcarbonyl($C_1$–$C_6$)alkyl groups; N—Z-amino($C_1$–$C_6$)alkylcarbonyl($C_1$–$_6$)alkyl groups; N—($C_1$–$C_6$)alkylamino($C_1$–$C_6$)alkylcarbonyl($C_1$–$C_6$) alkyl groups; N,N-di($C_1$–$C_6$)alkylamino($C_1$–$C_6$) alkylcarbonyl($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkylaminosulphonyl groups; N,N-di($C_1$–$_6$) alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$) alkyl groups; a carbamyl group; N—($C_1$–$_6$) alkylcarbamyl groups; N,N-di($C_1$–$C_6$)alkylcarbamyl groups; carbamyl($C_1$–$C_6$)alkyl groups; N—($C_1$–$C_6$) alkylcarbamyl($C_1$–$C_6$)alkyl groups; N,N-di($C_1$–$C_6$) alkylcarbamyl($C_1$–$_6$)alkyl group $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; and amino groups protected with at least one group chosen from ($C_1$–$C_6$) alkylcarbonyl groups, ($C_1$–$C_6$)alkylcarboxyl groups, trifluoro($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, ($C_1$–$C_6$)alkylcarboxyl groups, a carbamyl group, N—($C_1$–$C_6$)alkylcarbamyl groups, N,N-di($C_1$–$_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, a thiocarbamyl group, a formyl group, —CO—Z groups, and —CO—OZ groups;

$R_6$ is chosen from $C_1$–$C_6$ alkyl groups; $C_1$–$C_6$ monohydroxyalkyl groups; $C_2$–$C_6$ polyhydroxyalkyl groups; groups Z;($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$_6$)alkylaminosulphonyl-($C_1$–$C_6$)alkyl groups;($C_1$–$C_6$)alkylsulphinyl($C_1$–$C_6$)alkyl groups; ($C_1$–$C_6$)alkylsulphonyl($C_1$–$C_6$)alkyl groups;($C_1$–$C_6$) alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_1$–$_6$) alkylcarbonyl groups, ($C_1$–$C_6$)alkylcarboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, —CO—Z groups, and —CO—OZ groups;

$A_1$ is chosen from -$NR_4R_5$ groups and a hydroxyl group;

$A'_1$ is chosen from -$NR'_4R'_5$ groups and a hydroxyl group;

$A_2$ is chosen from -$NR_4R_5$ groups and a hydroxyl group;

$A'_2$ is chosen from -$NR'_4R'_5$ groups and a hydroxyl group;

$R_4$, $R_5$, $R_7$, $R_8$, $R'_4$, $R'_5$, $R'_7$ and $R'_8$, which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups; ($C_1$–$C_6$) alkoxy($C_1$–$C_6$)alkyl groups; aryl groups; a benzyl group; cyano($C_1$–$C_6$)alkyl groups; carbamyl($C_1$–$C_6$) alkyl groups; N—($C_1$–$C_6$)alkylcarbamyl($C_1$–$C_6$)alkyl groups; N,N-di($C_1$–$_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_1$–$_6$) alkylsulphinyl-($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups; $C_1$–$_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, $C_1$–$C_6$ alkylsulphonyl groups, a formyl group, trifluoro($C_1$–$C_6$)alkylcarbonyl groups, ($C_1$–$C_6$) alkylcarboxyl groups, thiocarbamyl groups, Z groups, —CO—Z groups, and —CO—OZ groups; one of the groups $R_4$, $R_5$, $R_7$ and $R_8$ one of the groups $R'_4$, $R'_5$, $R'_7$ and $R'_8$, or combinations thereof, which may be identical or different, are optionally chosen from ($C_1$–$C_6$) alkylcarboxyl groups;($C_1$–$C_6$)alkylcarbonyl groups; a formyl group; trifluoro($C_1$–$C_6$)alkylcarbonyl groups; amino($C_1$–$C_6$)alkylcarbonyl groups; N—Z-amino ($C_1$–$C_6$)alkylcarbonyl groups; N—($C_1$–$C_6$)alkylamino ($C_1$–$C_6$)alkylcarbonyl groups; N,N-di($C_1$–$_6$) alkylamino($C_1$–$C_6$)alkylcarbonyl groups; a carbamyl group; N—($C_1$–$C_6$)alkylcarbamyl groups; N,N-di ($C_1$–$C_6$)alkylcarbamyl groups; a thiocarbamyl group; an aminosulphonyl group; N—Z-aminosulphonyl groups; N—($C_1$–$C_6$)alkylaminosulphonyl groups; N,N-di($C_1$–$C_6$)alkylaminosulphonyl groups;($C_1$–$C_6$) alkylsulphonyl groups; —CO—Z groups; and —CO—OZ groups Z, which may be identical or different, is chosen from unsaturated cationic groups of formula (II), unsaturated cationic groups of formula (III), and saturated cationic groups of formula (IV):

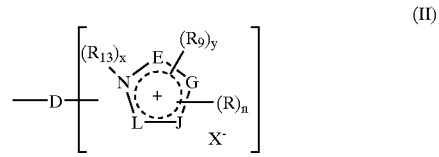

-continued

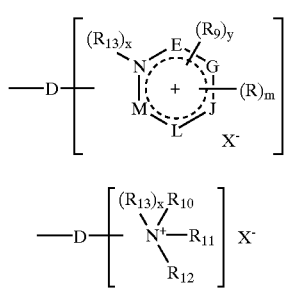

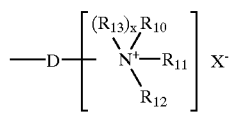

in which:

D is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;

ring members E, G, J, L and M, which may be identical or different, are each chosen from carbon, oxygen, sulphur, and nitrogen;

n is an integer chosen from 0 to 4 inclusive;

m is an integer chosen from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$) alkyl groups, an amino group, an aldehydo group, a carboxyl group, ($C_1$–$C_6$)alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR" groups and NR"R'" groups wherein R" and R'", which may be identical or different, are each chosen from $C_1$–$C_6$ alkyl groups, $C_1$–$C_6$ monohydroxyalkyl groups and $C_2$–$C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_9$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$)alkylsilane($C_{1-6}$)alkyl groups, ($C_1$–$C_6$)alkoxy($C_1$–$C_6$)alkyl groups, carbamyl-($C_1$–$C_6$)alkyl groups, ($C_{1-6}$) alkylcarboxy($C_1$–$C_6$-alkyl groups, and a benzyl group;

$R_{10}$, $R_{11}$ and $R_{12}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$) alkyl groups, aryl groups, a benzyl group, $C_1$–$C_6$ amidoalkyl groups, tri($C_1$–$C_6$)alkylsilane($C_{1-6}$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_{10}$, $R_{11}$ and $R_{12}$, can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, amino group, an aldehydo group, a carboxyl group, keto($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$) alkylcarbonyl groups, a carbamyl group and $C_1$–$C_6$ alkylsulphonyl groups;

$R_{13}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_{1-6}$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$) alkylcarboxy($C_1$–$C_6$)alkyl groups, ($C_1$–$C_6$) alkylsulphinyl($C_{1-6}$)alkyl groups, ($C_1$–$C_6$) alkylsulphonyl($C_1$–$C_6$)alkyl groups, ($C_1$–$C_6$)alkylketo ($C_1$–$C_6$)alkyl groups, N—($C_1$–$C_6$-alkylcarbamyl ($C_1$–$C_6$)alkyl groups, N—($C_1$–$C_6$)alkylsulphonamido ($C_{1-6}$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups;

x and y, which may be identical or different, are integers chosen from 0 and 1;

$X^-$ is chosen from a monovalent anion and a divalent anion; and provided that:

when Z is an unsaturated cationic group of formula (II):
if x=0, then said linker arm D is attached to said nitrogen atom other than E, G, J, and L,
if x=1, then said linker arm D is attached to one of said ring members chosen from E, G, J and L,
y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached;

when Z is an unsaturated cationic group of formula (III):
if x=0, then said linker arm D is attached to said nitrogen atom other than E, G, J, L, and M,
if x=1, then said linker arm D is attached to one of said ring members chosen from E, G, J, L, and M,
y=1 only when at least one of said ring members E, G, J, L and M is a divalent atom and $R_7$ is attached to said nitrogen atom of the unsaturated ring other than E, G, J, L and M; and when Z is a cationic group of formula (IV):
if x=0, then the linker arm D is attached to the nitrogen atom bearing said groups $R_8$, $R_9$ and $R_{10}$;
if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;

wherein at least one of $R_1$, $R_2$, $R_3$, $R_4$, $R_5$, $R_6$, $R_7$, $R_8$, $R'_1$, $R'_2$, $R'_3$, $R'_4$, $R'_5$, $R'_7$, and $R'_8$ comprises a Z group.

12. At least one coupler according to claim 11, wherein B is a linker arm comprising from 1 to 14 carbon atoms.

13. At least one coupler according to claim 11, wherein B is a linker arm interrupted by at least one heteroatom chosen from oxygen, sulphur, and nitrogen.

14. At least one coupler according to claim 11, wherein D is a linker arm comprising from 1 to 14 carbon atoms.

15. At least one coupler according to claim 11, wherein D is a linker arm interrupted by at least one heteroatom chosen from oxygen, sulphur, and nitrogen.

16. At least one coupler for oxidation dyeing of keratin fibres according to claim 11 wherein said keratin fibres are human keratin fibres.

17. At least one coupler for oxidation dyeing of keratin fibres according to claim 16 wherein said human keratin fibres are hair.

18. A composition for the oxidation dyeing of keratin fibres comprising, in a medium which is suitable for dyeing, at least one coupler chosen from compounds of formula (I) and acid addition salts thereof:

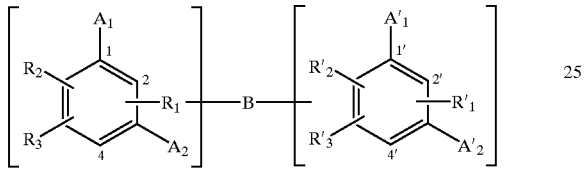

(I)

in which:

B is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;

$R_1$, $R_2$, $R_3$, $R'_1$, $R'_2$ and $R'_3$, which may be identical or different, are each chosen from hydrogen; halogens; Z groups; —CO—Z groups; —CO—OZ groups; ($C_1$–$C_6$) alkylcarbonyl groups; amino($C_1$–$C_6$)alkylcarbonyl groups; N—Z-amino($C_1$–$C_6$)alkylcarbonyl groups; N—($C_{1-6}$)alkyl-amino($C_1$–$C_6$)alkylcarbonyl groups; N,N-di($C_1$–$C_6$)alkylamino($C_{1-6}$)alkylcarbonyl groups; amino($C_1$–$C_6$)alkylcarbonyl($C_1$–$C_6$)alkyl groups; N—Z-amino($C_1$–$C_6$)alkylcarbonyl($C_{1-6}$)alkyl groups; N—($C_1$–$C_6$)alkylamino($C_1$–$C_6$)alkylcarbonyl($C_1$–$C_6$) alkyl groups; N,N-di($C_1$–$C_6$)alkylamino($C_1$–$C_6$) alkylcarbonyl($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkylaminosulphonyl groups; N,N-di($C_{1-6}$) alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$) alkyl groups; a carbamyl group; N—($C_{1-6}$) alkylcarbamyl groups; N,N-di($C_1$–$C_6$)alkylcarbamyl groups; carbamyl($C_1$–$C_6$)alkyl groups; N—($C_1$–$C_6$) alkylcarbamyl($C_1$–$C_6$)alkyl groups; N,N-di($C_1$–$C_6$) alkylcarbamyl($C_{1-6}$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; and amino groups protected with at least one group chosen from ($C_1$–$C_6$) alkylcarbonyl groups, ($C_1$–$C_6$)alkylcarboxyl groups, trifluoro($C_1$–$C_6$)alkylcarbonyl groups, amino($C_1$–$C_6$) alkylcarbonyl groups, N—Z-amino($C_1$–$C_6$) alkylcarbonyl groups, N—($C_1$–$C_6$)alkylamino($C_1$–$C_6$) alkylcarbonyl groups, N,N-di($C_1$–$C_6$)alkylamino ($C_1$–$C_6$)alkylcarbonyl groups, ($C_1$–$C_6$)alkylcarboxyl groups, a carbamyl group, N—($C_1$–$C_6$)alkylcarbamyl groups, N,N-di($C_1$–$C_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$) alkylaminosulphonyl groups, a thiocarbamyl group, a formyl group, —CO—Z groups, and —CO—OZ groups;

$R_6$ is chosen from $C_1$–$C_6$ alkyl groups; $C_1$–$C_6$ monohydroxyalkyl groups; $C_2$–$C_6$ polyhydroxyalkyl groups; groups Z;($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_{1-6}$)alkylcarbamyl($C_1$–$C_6$)alkyl groups; N,N-di ($C_1$–$C_6$)alkylcarbamyl($C_1$–$C_6$)alkyl groups; $C_{1-6}$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_{1-6}$)alkylaminosulphonyl-($C_1$–$C_6$)alkyl groups;($C_1$–$C_6$)alkylsulphinyl($C_1$–$C_6$)alkyl groups; ($C_1$–$C_6$)alkylsulphonyl($C_1$–$C_6$)alkyl groups;($C_1$–$C_6$) alkylcarbonyl($C_{1-6}$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_{1-6}$) alkylcarbonyl groups, ($C_1$–$C_6$)alkylcarboxy groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, —CO—Z groups, and —CO—OZ groups;

$A_1$ is chosen from-$NR_4R_5$ groups and a hydroxyl group;
$A'_1$ is chosen from-$NR'_4R'_5$ groups and a hydroxyl group;
$A_2$ is chosen from-$NR_4R_5$ groups and a hydroxyl group;
$A'_2$ is chosen from-$NR'_4R'_5$ groups and a hydroxyl group;
$R_4$, $R_5$, $R_7$, $R_8$, $R'_4$, $R'_5$, $R'_7$ and $R'_8$,which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups; ($C_1$–$C_6$) alkoxy($C_1$–$C_6$)alkyl groups; aryl groups; a benzyl group; cyano($C_1$–$C_6$)alkyl groups; carbamyl($C_1$–$C_6$) alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_{1-6}$) alkylsulphinyl-($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$)

alkylcarbamyl groups, N,N-di($C_1$–$C_6$)alkylcarbamyl groups, $C_1$–$C_6$ alkylsulphonyl groups, a formyl group, trifluoro($C_1$–$C_6$)alkylcarbonyl groups, ($C_1$–$C_6$) alkylcarboxyl groups, thiocarbamyl groups, Z groups, —CO—Z groups, and —CO—OZ groups;

one of the groups $R_4$, $R_5$, $R_7$ and $R_8$ or one of the groups $R'_4$, $R'_5$, $R'_7$ and $R'_8$, or combinations thereof, which may be identical or different, are optionally chosen from ($C_1$–$C_6$)alkylcarboxyl groups; ($C_1$–$C_6$) alkylcarbonyl groups; a formyl group; trifluoro($C_1$–$C_6$) alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; a carbamyl group; N—($C_1$–$C_6$)alkylcarbamyl groups; N,N-di($C_1$–$C_6$)alkylcarbamyl groups; a thiocarbamyl group; an aminosulphonyl group; N—Z-aminosulphonyl groups; N—($C_1$–$C_6$) alkylaminosulphonyl groups; N,N-di($C_1$–$C_6$) alkylaminosulphonyl groups;($C_1$–$C_6$)alkylsulphonyl groups; —CO—Z groups; and —CO—OZ groups Z, which may be identical or different, is chosen from unsaturated cationic groups of formula (II), unsaturated cationic groups of formula (III), and saturated cationic groups of formula (IV):

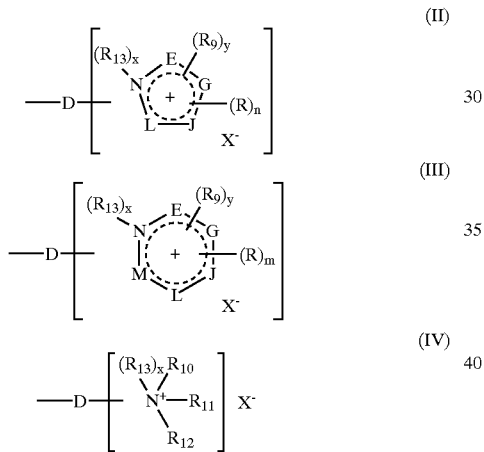

in which:

D is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;

ring members E, G, J, L and M, which may be identical or different, are each chosen from carbon, oxygen, sulphur, and nitrogen;

n is an integer chosen from 0 to 4 inclusive;

m is an integer chosen from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$) alkyl groups, an amido group, an aldehydo group, a carboxyl group, ($C_1$–$C_6$)alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR" groups and NR"R"' groups wherein R" and R"', which may be identical or different, are each chosen from $C_1$–$C_6$ alkyl groups, $C_1$–$C_6$ monohydroxyalkyl groups and $C_2$–$C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_9$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$)alkylsilane ($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$) alkylcarboxy($C_1$–$C_6$)alkyl groups, and a benzyl group;

$R_{10}$, $R_1$, and $R_{12}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$) alkyl groups, aryl groups, a benzyl group, $C_1$–$C_6$ amidoalkyl groups, tri($C_1$–$C_6$)alkylsilane($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_{10}$, $R_{11}$ and $R_{12}$, can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri ($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

$R_{13}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$) alkylcarboxy($C_1$–$C_6$)alkyl groups, ($C_1$–$C_6$) alkylsulphinyl($C_1$–$C_6$)alkyl groups, ($C_1$–$C_6$) alkylsulphonyl($C_1$–$C_6$)alkyl groups, ($C_1$–$C_6$)alkylketo ($C_1$–$C_6$)alkyl groups, N—($C_1$–$C_6$)alkylcarbamyl ($C_1$–$C_6$)alkyl groups, N—($C_1$–$C_6$)alkylsulphonamido ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups;

x and y, which may be identical or different, are integers chosen from 0 and 1;

$X^-$ is chosen from a monovalent anion and a divalent anion; and provided that:

when Z is an unsaturated cationic group of formula (II):

if x=0, then said linker arm D is attached to said nitrogen atom other than E, G, J, and L, if x=1, then said linker arm D is attached to one of said ring members chosen from E, G, J and L, y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached;

when Z is an unsaturated cationic group of formula (III):

if x=0, then said linker arm D is attached to said nitrogen atom other than E, G, J, L, and M, if x=1, then said linker arm D is attached to one of said ring members chosen from E, G, J, L, and M, y=1 only when at least one of said ring members E, G, J, L and M is a divalent atom and $R_7$ is attached to said nitrogen atom of the unsaturated ring other than E, G, J, L and M; and when Z is a cationic group of formula (IV):

if x=0, then the linker arm D is attached to the nitrogen atom bearing said groups $R_8$, $R_9$ and $R_{10}$;

if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;

wherein at least one of $R_1$, $R_2$, $R_3$, $R_4$, $R_5$, $R_6$, $R_7$, $R_8$, $R'_1$, $R'_2$, $R'_3$, $R'_4$, $R'_5$, $R'_7$, and $R'_8$ comprises a Z group.

19. A composition according to claim 18, wherein B is a linker arm comprising from 1 to 14 carbon atoms.

20. A composition according to claim 18, wherein B is a linker arm interrupted by at least one heteroatom chosen from oxygen, sulphur, and nitrogen.

21. A composition according to claim 18, wherein D is a linker arm comprising from 1 to 14 carbon atoms.

22. A composition according to claim 18, wherein D is a linker arm interrupted by at least one heteroatom chosen from oxygen, sulphur, and nitrogen.

23. A composition for the oxidation dyeing of keratin fibres according to claim 18, wherein said medium is chosen from water and a mixture of water and at least one organic solvent chosen from $C_{1-4}$ lower alkanols, glycerol, glycols, glycol ethers, and aromatic alcohols.

24. A composition for the oxidation dyeing of keratin fibres according to claim 23, wherein said at least one organic solvent may be present in proportions ranging from about 1% to 40% by weight relative to the total weight of said compositions.

25. A composition for the oxidation dyeing of keratin fibres according to claim 18, wherein said at least one coupler is present in a concentration ranging from 0.0005 to 12% by weight relative to the total weight of said composition.

26. A composition for the oxidation dyeing of keratin fibres according to claim 25 wherein said concentration ranges from 0.005% to 6% by weight relative to the total weight of said composition.

27. A composition for the oxidation dyeing of keratin fibres according to claim 18, further comprising at least one oxidation base chosen from para-phenylenediamine bases, bis(phenyl)alkylenediamine bases, para-aminophenol bases, ortho-aminophenol bases, heterocyclic bases, and acid addition salts thereof.

28. A composition for the oxidation dyeing of keratin fibres according to claim 27, wherein said para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N—(β-hydroxypropyl)-para-phenylenediamine, 2-hydroxymethyl-para-phenylenediamine, N,N-dimethyl-3-methyl-para-phenylenediamine, N-ethyl-N—(β-hydroxyethyl)-para-phenylenediamine, N—(β,y-dihydroxypropyl)-para-phenylenediamine, N—(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N—(β-methoxyethyl)-para-phenylenediamine, and acid addition salts thereof.

29. A composition for the oxidation dyeing of keratin fibres according to claim 27, wherein said bis(phenyl)alkylenediamines are chosen from N,NN-bis(β-hydroxyethyl)-N,NN-bis(4N-aminophenyl)-1,3-diaminopropanol, N,NN-bis(β-hydroxyethyl)-N,NN-bis(4N-aminophenyl)ethylenediamine, N,NN-bis(4-aminophenyl)tetramethylenediamine, N,NN-bis(β-hydroxyethyl)-N,NN-bis(4-aminophenyl) tetramethylenediamine, N,NN-bis(4-methylaminophenyl) tetramethylenediamine, N,NN-bis(ethyl)-N,NN-bis(4N-amino-3N-methylphenyl)ethylenediamine, 1,8-bis(2,5-diaminophenoxy)-3,5-dioxaoctane, and acid addition salts thereof.

30. A composition for the oxidation dyeing of keratin fibres according to claim 27, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

31. A composition for the oxidation dyeing of keratin fibres according to claim 27, wherein said ortho-aminophenols are chosen from 2-aminophenol, 2-amino-5-methylphenol, 2-amino-6-methylphenol, 5-acetamido-2-aminohenol, and acid addition salts thereof.

32. A composition for the oxidation dyeing of keratin fibres according to claim 27, wherein said heterocyclic bases are chosen from pyridine derivatives, pyrimidine derivatives and pyrazole derivatives.

33. A composition for the oxidation dyeing of keratin fibres according to claim 27, wherein said at least one oxidation base is present in a concentration ranging from 0.0005 to 12% by weight relative to the total weight of said composition.

34. A composition for the oxidation dyeing of keratin fibres according to claim 33, wherein said concentration ranges from 0.005% to 6% by weight relative to the total weight of said composition.

35. A composition for the oxidation dyeing of keratin fibres according to claim 18, further comprising at least one second coupler other than said at least one coupler.

36. A composition for the oxidation dyeing of keratin fibres according to claim 35, wherein said at least one second coupler is chosen from meta-phenylenediamines, meta-aminophenols, meta-diphenols, heterocyclic couplers, and acid addition salts thereof.

37. A composition for the oxidation dyeing of keratin fibres according to claim 35, wherein said at least one second coupler is chosen from 2-methyl-5-aminophenol, 5-N—(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one and acid addition salts thereof.

38. A composition for the oxidation dyeing of keratin fibres according to claim 35, wherein said at least one second coupler is present in a concentration ranging from 0.0001% to 10% by weight relative to the total weight of said composition.

39. A composition for the oxidation dyeing of keratin fibres according to claim 38, wherein said concentration ranges from 0.005% to 5% by weight relative to the total weight of said composition.

40. A composition for the oxidation dyeing of keratin fibres according to claim 18, further comprising at least one direct dye.

41. A composition for the oxidation dyeing of keratin fibres according to claim 18, further comprising at least one adjuvant chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, packaging agents, silicones, film-forming agents, ceramides, preserving agents and opacifiers.

42. A composition for the oxidation dyeing of keratin fibres according to claim 18, further comprising at least one agent chosen from acidifying agents and basifying agents.

43. A composition for the oxidation dyeing of keratin fibres according to claim 18, having a pH ranging from 3 to 12.

44. A composition for the oxidation dyeing of keratin fibres according to claim 18, wherein said composition is in a form chosen from liquids, creams and gels.

45. A composition for the oxidation dyeing of keratin fibres according to claim 18, wherein said acid addition salt is chosen from a hydrochloride, a hydrobromide, a sulphate, a citrate, a succinate, a tartrate, a lactate and an acetate.

46. A process for oxidation dyeing of at least one keratin fibre, comprising applying to said keratin fibre at least one dye composition for a time sufficient to develop a coloration and also applying to said keratin fibre at least one oxidizing agent, said at least one oxidizing agent and said at least one dye composition being applied to said keratin fibres at the same time, either together or separately, or said at least one oxidizing agent and said at least one dye composition being applied sequentially to said keratin fibres, said at least one dye composition comprising, in a medium which is suitable for dyeing, at least one coupler chosen from compounds of formula (I) and acid addition salts thereof:

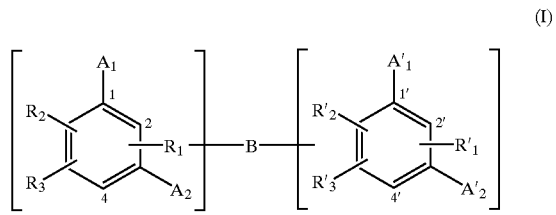

(I)

in which:

B is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$-$C_6$ alkoxy groups;

$R_1$, $R_2$, $R_3$, $R'_1$, $R'_2$ and $R'_3$, which may be identical or different, are each chosen from hydrogen; halogens; Z groups; —CO—Z groups; —CO—OZ groups; ($C_1$-$C_6$) alkylcarbonyl groups; amino($C_1$-$C_6$)alkylcarbonyl groups; N—Z-amino($C_1$-$C_6$)alkylcarbonyl groups; N—($C_1$-$C_6$)alkylamino($C_1$-$C_6$)alkylcarbonyl groups; N,N-di($C_1$-$C_6$)alkylamino($C_1$-$C_6$)alkylcarbonyl groups; amino($C_1$-$C_6$)alkylcarbonyl($C_1$-$C_6$)alkyl groups; N—Z-amino($C_1$-$C_6$)alkylcarbonyl($C_1$-$C_6$) alkyl groups; N—($C_1$-$C_6$)alkylamino($C_1$-$C_6$) alkylcarbonyl($C_1$-$C_6$)alkyl groups; N,N-di($C_1$-$C_6$) alkylamino($C_1$-$C_6$)alkylcarbonyl($C_1$-$C_6$)alkyl groups; a carboxyl group; ($C_1$-$C_6$)alkylcarboxyl groups; $C_1$-$C_6$ alkylsulphonyl groups; aminosulphonyl groups; N—Z-aminosulphonyl groups; $C_1$-$C_6$ N-alkylaminosulphonyl groups; N,N-di($C_1$-$C_6$) alkylaminosulphonyl groups; $C_1$-$C_6$ aminosulphonylalkyl groups; $C_1$-$C_6$ N—Z-aminosulphonylalkyl groups; N—($C_1$-$C_6$)alkylaminosulphonyl($C_1$-$C_6$)alkyl groups; N,N-di($C_1$-$C_6$)alkylaminosulphonyl($C_1$-$C_6$) alkyl groups; a carbamyl group; N—($C_1$-$C_6$)alkylcarbamyl groups; N,N-di($C_1$-$C_6$)alkylcarbamyl groups; carbamyl($C_1$-$C_6$)alkyl groups; N—($C_1$-$C_6$) alkylcarbamyl($C_1$-$C_6$)alkyl groups; N,N-di($C_1$-$C_6$) alkylcarbamyl($C_1$-$C_6$)alkyl group $C_1$-$C_6$ alkyl groups; $C_1$-$C_6$ monohydroxyalkyl groups; $C_2$-$C_6$ polyhydroxyalkyl groups; ($C_1$-$C_6$)alkoxy($C_1$-$C_6$)alkyl groups; $C_1$-$C_6$ trifluoroalkyl groups; a cyano group; groups —$OR_6$; groups —$SR_6$; and amino groups protected with at least one group chosen from ($C_1$-$C_6$) alkylcarbonyl groups, ($C_1$-$C_6$)alkylcarboxyl groups, trifluoro($C_1$-$C_6$)alkylcarbonyl groups, amino($C_1$-$C_6$) alkylcarbonyl groups, N—Z-amino($C_1$-$C_6$) alkylcarbonyl groups, N—($C_1$-$C_6$)alkylamino($C_1$-$C_6$) alkylcarbonyl groups, N,N-di($C_1$-$C_6$)alkylamino ($C_1$-$C_6$)alkylcarbonyl groups, ($C_1$-$C_6$)alkylcarboxyl groups, a carbamyl group, N—($C_1$-$C_6$)alkylcarbamyl groups, N,N-di($C_1$-$C_6$)alkylcarbamyl groups, $C_1$-$C_6$ alkylsulphonyl groups, aminosulphonyl groups, N—Z-aminosulphonyl groups, $C_1$-$C_6$ N-alkylaminosulphonyl groups, N,N-di($C_1$-$C_6$) alkylaminosulphonyl groups, a thiocarbamyl group, a formyl group, —CO—Z groups, and —CO—OZ groups;

$R_6$ is chosen from $C_1$-$C_6$ alkyl groups; $C_1$-$C_6$ monohydroxyalkyl groups; $C_2$-$C_6$ polyhydroxyalkyl groups; groups Z;($C_1$-$C_6$)alkoxy($C_1$-$C_6$)alkyl groups; aryl groups; a benzyl group; carboxy($C_1$-$C_6$)alkyl groups;

($C_1$–$C_6$)alkylcarboxy-($C_1$–$C_6$)alkyl groups; cyano($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl-($C_1$–$C_6$)alkyl groups;($C_1$–$C_6$)alkylsulphinyl($C_1$–$C_6$)alkyl groups; ($C_1$–$C_6$)alkylsulphonyl($C_1$–$C_6$)alkyl groups;($C_1$–$C_6$) alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_1$–$C_6$)alkylcarbonyl groups, ($C_1$–$C_6$)alkylcarboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, —CO—Z groups, and —CO—OZ groups;

$A_1$ is chosen from -$NR_4R_5$ groups and a hydroxyl group;
$A'_1$ is chosen from -$NR'_4R'_5$ groups and a hydroxyl group;
$A_2$ is chosen from -$NR_4R_5$ groups and a hydroxyl group;
$A'_2$ is chosen from -$NR'_4R'_5$ groups and a hydroxyl group;
$R_4$, $R_5$, $R_7$, $R_8$, $R'_4$, $R'_5$, $R'_7$ and $R'_8$, which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups; ($C_1$–$C_6$) alkoxy($C_1$–$C_6$)alkyl groups; aryl groups; a benzyl group; cyano($C_1$–$C_6$)alkyl groups; carbamyl($C_1$–$C_6$) alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_1$–$C_6$) alkylsulphinyl-($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, $C_1$–$C_6$ alkylsulphonyl groups, a formyl group, trifluoro($C_1$–$C_6$)alkylcarbonyl groups, ($C_1$–$C_6$) alkylcarboxyl groups, thiocarbamyl groups, Z groups, —CO—Z groups, and —CO—OZ groups;

one of the groups $R_4$, $R_5$, $R_7$ and $R_8$ or one of the groups $R'_4$, $R'_5$, $R'_7$ and $R'_8$, or combinations thereof, which may be identical or different, are optionally chosen from ($C_1$–$C_6$)alkylcarboxyl groups;($C_1$–$C_6$) alkylcarbonyl groups; a formyl group; trifluoro($C_1$–$C_6$) alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; a carbamyl group; N—($C_1$–$C_6$)alkylcarbamyl groups; N,N-di($C_1$–$C_6$)alkylcarbamyl groups; a thiocarbamyl group; an aminosulphonyl group; N—Z-aminosulphonyl groups; N—($C_1$–$C_6$) alkylaminosulphonyl groups; N,N-di($C_1$–$C_6$) alkylaminosulphonyl groups;($C_1$–$C_6$)alkylsulphonyl groups; —CO—Z groups; and—CO—OZ groups Z, which may be identical or different, is chosen from unsaturated cationic groups of formula (II), unsaturated cationic groups of formula (III), and saturated cationic groups of formula (IV):

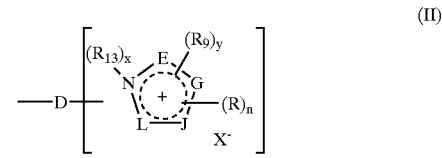

(II)

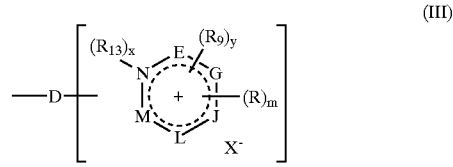

(III)

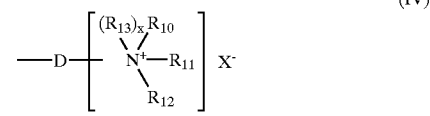

(IV)

in which:
D is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;

ring members E, G, J, L and M, which may be identical or different, are each chosen from carbon, oxygen, sulphur, and nitrogen;

n is an integer chosen from 0 to 4 inclusive;
m is an integer chosen from 0 to 5 inclusive;
the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$) alkyl groups, an amido group, an aldehydo group, a carboxyl group, ($C_1$–$C_6$)alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR" groups and NR"R'" groups wherein R" and R'", which may be identical or different, are each chosen from $C_1$–$C_6$ alkyl groups, $C_1$–$C_6$ monohydroxyalkyl groups and $C_2$–$C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_9$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$)alkylsilane ($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$) alkylcarboxy($C_1$–$C_6$) alkyl groups, and a benzyl group;

$R_{10}$, $R_{11}$ and $R_{12}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$) alkyl groups, aryl groups, a benzyl group, $C_1$–$C_6$ amidoalkyl groups, tri($C_1$–$C_6$)alkylsilane($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_{10}$, $R_{11}$ and $R_{12}$, can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri ($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

$R_{13}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$) alkylcarboxy($C_1$–$C_6$)alkyl groups, ($C_1$–$C_6$) alkylsulphinyl($C_1$–$C_6$)alkyl groups, ($C_1$–$C_6$) alkylsulphonyl($C_1$–$C_6$)alkyl groups, ($C_1$–$C_6$)alkylketo ($C_1$–$C_6$)alkyl groups, N—($C_1$–$C_6$)alkylcarbamyl ($C_1$–$C_6$)alkyl groups, N—($C_1$–$C_6$)alkylsulphonamido ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups;

x and y, which may be identical or different, are integers chosen from 0 and 1;

$X^-$ is chosen from a monovalent anion and a divalent anion; and provided that:

when Z is an unsaturated cationic group of formula (II):
  if x=0, then said linker arm D is attached to said nitrogen atom other than E, G, J, and L,
  if x=1, then said linker arm D is attached to one of said ring members chosen from E, G, J and L, y=1 only when:
   1) said ring members E, G, J, and L are all simultaneously carbon atoms and $R_7$ is attached to said nitrogen atom of the unsaturated ring; or alternatively
   2) at least one of the ring members E, G, J, and L is a nitrogen atom to which $R_7$ is attached;

when Z is an unsaturated cationic group of formula (III):
  if x=0, then said linker arm D is attached to said nitrogen atom other than E, G, J, L, and M,
  if x=1, then said linker arm D is attached to one of said ring members chosen from E, G, J, L, and M, y=1 only when at least one of said ring members E, G, J, L and M is a divalent atom and $R_7$ is attached to said nitrogen atom of the unsaturated ring other than E, G, J, L and M; and when Z is a cationic group of formula (IV):
  if x=0, then the linker arm D is attached to the nitrogen atom bearing said groups $R_8$, $R_9$ and $R_{10}$;
  if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;

wherein at least one of $R_1$, $R_2$, $R_3$, $R_4$, $R_5$, $R_6$, $R_7$, $R_8$, $R'_1$, $R'_2$, $R'_3$, $R'_5$, $R'_7$, and $R'_8$ comprises a Z group.

47. A process according to claim 46, wherein B is a linker arm comprising from 1 to 14 carbon atoms.

48. A process according to claim 46, wherein B is a linker arm interrupted by at least one heteroatom chosen from oxygen, sulphur, and nitrogen.

49. A process according to claim 46, wherein D is a linker arm comprising from 1 to 14 carbon atoms.

50. A process according to claim 46, wherein D is a linker arm interrupted by at least one heteroatom chosen from oxygen, sulphur, and nitrogen.

51. A process according to claim 46, wherein said at least one oxidizing agent is chosen from hydrogen peroxide, urea peroxide, alkali metal bromates, persalts, and enzymes.

52. A process according to claim 51, wherein said persalts are chosen from perborates and persulphates.

53. A process according to claim 51, wherein said enzymes are chosen from peroxidases and 2-electron oxidoreductases.

54. A multi-compartment dyeing "kit", comprising a first compartment containing at least one dye composition, and a second compartment containing at least one oxidizing agent, wherein said at least one dye composition comprises, in a medium which is suitable for dyeing, at least one coupler chosen from compounds of formula (I) and acid addition salts thereof:

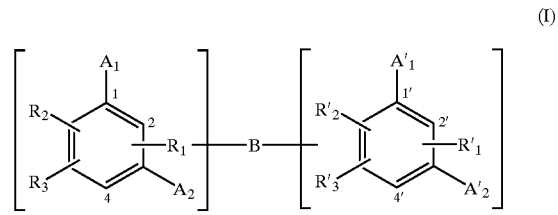

(I)

in which:
B is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;

$R_1$, $R_2$, $R_3$, $R'_1$, $R'_2$ and $R'_3$, which may be identical or different, are each chosen from hydrogen; halogens; Z groups; —CO—Z groups; —CO—OZ groups; ($C_1$–$C_6$) alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; amino($C_1$–$C_6$)alkylcarbonyl($C_1$–$C_6$)alkyl groups; N—Z-amino($C_1$–$C_6$)alkylcarbonyl($C_1$–$C_6$) alkyl groups; N—($C_1$–$C_6$)alkylamino($C_1$–$C_6$) alkylcarbonyl($C_1$–$C_6$)alkyl groups; N,N-di($C_1$–$C_6$) alkylamino($C_1$–$C_6$)alkylcarbonyl($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkylaminosulphonyl groups; N,N-di($C_1$–$C_6$)alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups; a carbamyl group; N—($C_1$–$C_6$)alkylcarbamyl groups; N,N-di($C_1$–$C_6$)alkylcarbamyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; and amino groups protected with at least one group chosen from ($C_1$–$C_6$)alkylcarbonyl groups, ($C_1$–$C_6$)alkylcarboxyl groups, trifluoro($C_1$–$C_6$)alkylcarbonyl groups, amino($C_1$–$C_6$)alkylcarbonyl groups, N—Z-amino($C_1$–$C_6$)alkylcarbonyl groups, N—($C_1$–$C_6$)alkylamino($C_1$–$C_6$)alkylcarbonyl groups, N,N-di($C_1$–$C_6$)alkylamino($C_1$–$C_6$)alkylcarbonyl groups, ($C_1$–$C_6$)alkylcarboxyl groups, a carbamyl group, N—($C_1$–$C_6$)alkylcarbamyl groups, N,N-di($C_1$–$C_6$)alkylcarbamyl groups, $C_1$–$C_6$ alkylsulphonyl groups, aminosulphonyl groups, N—Z-aminosulphonyl groups, $C_1$–$C_6$ N-alkylaminosulphonyl groups, N,N-di($C_1$–$C_6$)alkylaminosulphonyl groups, a thiocarbamyl group, a formyl group, —CO—Z groups, and —CO—OZ groups;

$R_6$ is chosen from $C_1$–$C_6$ alkyl groups; $C_1$–$C_6$ monohydroxyalkyl groups; $C_2$–$C_6$ polyhydroxyalkyl groups; groups Z;($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups;($C_1$–$C_6$)alkylsulphinyl($C_1$–$C_6$)alkyl groups; ($C_1$–$C_6$)alkylsulphonyl($C_1$–$C_6$)alkyl groups;($C_1$–$C_6$) alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_1$–$C_6$)alkylcarbonyl groups, ($C_1$–$C_6$)alkylcarboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, —CO—Z groups, and —CO—OZ groups;

$A_1$ is chosen from-$NR_4R_5$ groups and a hydroxyl group;

$A'_1$ is chosen from-$NR'_4R'_5$ groups and a hydroxyl group;

$A_2$ is chosen from-$NR_4R_5$ groups and a hydroxyl group;

$A'_2$ is chosen from-$NR'_4R'_5$ groups and a hydroxyl group;

$R_4$, $R_5$, $R_7$, $R_8$, $R'_4$, $R'_5$, $R'_7$ and $R'_8$, which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups;($C_1$–$C_6$) alkoxy($C_1$–$C_6$)alkyl groups; aryl groups; a benzyl group; cyano($C_1$–$C_6$)alkyl groups; carbamyl($C_1$–$C_6$) alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_1$–$C_6$)alkylsulphinyl($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups; $C_1$–$C_6$ aminoalkyl groups wherein said amino is substituted with one or two groups chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, $C_1$–$C_6$ alkylsulphonyl groups, a formyl group, trifluoro($C_1$–$C_6$)alkylcarbonyl groups, ($C_1$–$C_6$) alkylcarboxyl groups, thiocarbamyl groups, Z groups, —CO—Z groups, and —CO—OZ groups;

one of the groups $R_4$, $R_5$, $R_7$ and $R_8$ or one of the groups $R'_4$, $R'_5$, $R'_7$ and $R'_8$, or combinations thereof, which may be identical or different, are optionally chosen from ($C_1$–$C_6$)alkylcarboxyl groups; ($C_1$–$C_6$) alkylcarbonyl groups; a formyl group; trifluoro($C_1$–$C_6$) alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; a carbamyl group; N—($C_1$–$C_6$)alkylcarbamyl groups; N,N-di($C_1$–$C_6$)alkylcarbamyl groups; a thiocarbamyl group; an aminosulphonyl group; N—Z-aminosulphonyl groups; N—($C_1$–$C_6$) alkylaminosulphonyl groups; N,N-di($C_1$–$C_6$) alkylaminosulphonyl groups;($C_1$–$C_6$)alkylsulphonyl groups; —CO—Z groups; and—CO—OZ groups Z, which may be identical or different, is chosen from unsaturated cationic groups of formula (II), unsaturated cationic groups of formula (III), and saturated cationic groups of formula (IV):

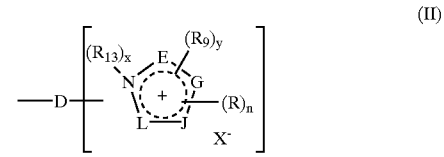

(II)

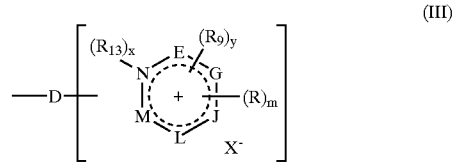

(III)

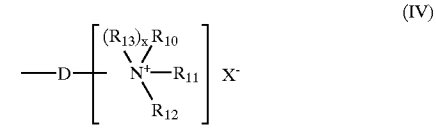

(IV)

in which:

D is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups;

ring members E, G, J, L and M, which may be identical or different, are each chosen from carbon, oxygen, sulphur, and nitrogen;

n is an integer chosen from 0 to 4 inclusive;

m is an integer chosen from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$) alkyl groups, an amido group, an aldehydo group, a carboxyl group, ($C_1$–$C_6$)alkylcarbonyl groups, a thio group, $C_1$–$C_6$ thioalkyl groups, $C_1$–$C_6$ alkylthio groups, an amino group, amino groups protected with at least one group chosen from $C_1$–$C_6$ alkylcarbonyl groups, a carbamyl group, and $C_1$–$C_6$ alkylsulphonyl groups, and NHR" groups and NR"R'" groups wherein R" and R'", which may be identical or different, are each chosen from $C_1$–$C_6$ alkyl groups, $C_1$–$C_6$ monohydroxyalkyl groups and $C_2$–$C_6$ polyhydroxyalkyl groups;

when n is greater than or equal to 2, two of the adjacent R groups may also form together an unsaturated ring chosen from 5- and 6-membered carbon-based rings and rings containing at least one hetero atom;

$R_9$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$)alkylsilane($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$) alkylcarboxy($C_1$–$C_6$)alkyl groups, and a benzyl group;

$R_{10}$, $R_{11}$ and $R_{12}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$) alkyl groups, aryl groups, a benzyl group, $C_1$–$C_6$ amidoalkyl groups, tri($C_1$–$C_6$)alkylsilane($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_{10}$, $R_{11}$ and $R_{12}$, can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri ($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

$R_{13}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$) alkylcarboxy($C_1$–$C_6$)alkyl groups, ($C_1$–$C_6$) alkylsulphinyl($C_1$–$C_6$)alkyl group ($C_1$–$C_6$) alkylsulphonyl($C_1$–$C_{1-6}$)alkyl groups, ($C_1$–$C_6$) alkylketo($C_1$–$C_6$)alkyl groups, N—($C_1$–$C_6$)- alkylcarbamyl($C_1$–$C_6$)alkyl groups, N—($C_1$–$C_6$) alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups;

x and y, which may be identical or different, are integers chosen from 0 and 1;

$X^-$ is chosen from a monovalent anion and a divalent anion; and provided that:

when Z is an unsaturated cationic group of formula (II):
if x=0, then said linker arm D is attached to said nitrogen atom other than E, G, J, and L,
if x=1, then said linker arm D is attached to one of said ring members chosen from E, G, J and L,
y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached;

when Z is an unsaturated cationic group of formula (III):
if x=0, then said linker arm D is attached to said nitrogen atom other than E, G, J, L, and M,
if x=1, then said linker arm D is attached to one of said ring members chosen from E, G, J, L, and M,
y=1 only when at least one of said ring members E, G, J, L and M is a divalent atom and $R_7$ is attached to said nitrogen atom of the unsaturated ring other than E, G, J, L and M; and when Z is a cationic group of formula (IV):
if x=0, then the linker arm D is attached to the nitrogen atom bearing said groups $R_8$, $R_9$ and $R_{10}$;
if x=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring;

wherein at least one of $R_1$, $R_2$, $R_3$, $R_4$, $R_5$, $R_6$, $R_7$, $R_8$, $R'_1$, $R'_2$, $R'_3$, $R'_4$, $R'_5$, $R'_7$, and $R'_8$ comprises a Z group.

55. A kit according to claim 54, wherein B is a linker arm comprising from 1 to 14 carbon atoms.

56. A kit according to claim 54, wherein B is a linker arm interrupted by at least one heteroatom chosen from oxygen, sulphur, and nitrogen.

57. A kit according to claim 54, wherein D is a linker arm comprising from 1 to 14 carbon atoms.

58. A kit according to claim 54, wherein D is a linker arm interrupted by at least one heteroatom chosen from oxygen, sulphur, and nitrogen.

* * * * *

UNITED STATES PATENT AND TRADEMARK OFFICE
CERTIFICATE OF CORRECTION

PATENT NO. : 6,451,068 B1
DATED : September 17, 2002
INVENTOR(S) : Alain Genet et al.

It is certified that error appears in the above-identified patent and that said Letters Patent is hereby corrected as shown below:

Column 16,
Lines 10 and 51, "amino" should read -- amido --.
Line 18, "$C_1$-," should read -- $C_1$-$C_6$ --.

Column 19,
Lines 24-25, "N,N-di($C_1$-$C_6$)alkylcarbamyl($C_{1-6}$)alkyl group" should read
-- N,N-di($C_1$-$C_6$)alkylcarbamyl($C_1$-$C_6$)alkyl groups; --.

Column 20,
Line 38, after "$R_8$" insert -- or --.

Column 21,
Line 36, "amino" should read -- amido --.

Column 22,
Line 9, "amino" should read -- an amido --.

Column 26,
Line 20, "$R_1$," should read -- $R_{11}$ --.

Column 28,
Lines 18-19, "N-(β,y-dihydroxypropyl)-para-phenylenediamine" should read
-- N-(β,γ-dihydroxypropyl)-para-phenylenediamine --.

Column 30,
Line 44, "group" should read -- groups; --.

UNITED STATES PATENT AND TRADEMARK OFFICE
CERTIFICATE OF CORRECTION

PATENT NO. : 6,451,068 B1
DATED : September 17, 2002
INVENTOR(S) : Alain Genet et al.

It is certified that error appears in the above-identified patent and that said Letters Patent is hereby corrected as shown below:

Column 34,
Line 10, after $R'_3$," insert -- $R'_4$, --.

Column 38,
Line 7, "group" should read -- group; --.

Signed and Sealed this

Fifth Day of April, 2005

JON W. DUDAS
*Director of the United States Patent and Trademark Office*